United States Patent [19]
Burckhardt et al.

[11] 4,242,912
[45] Jan. 6, 1981

[54] METHOD AND APPARATUS FOR PRODUCING CROSS-SECTIONAL IMAGES USING ULTRASOUND

[75] Inventors: Christoph B. Burckhardt, Muttenz; Pierre-André Grandchamp, Münchenstein, both of Switzerland; Heinz Hoffmann, Grenzach, Fed. Rep. of Germany; Rainer Fehr, Reinach, Switzerland

[73] Assignee: Hoffmann-La Roche Inc., Nutley, N.J.

[21] Appl. No.: 11,005

[22] Filed: Feb. 9, 1979

Related U.S. Application Data

[63] Continuation of Ser. No. 844,092, Mar. 6, 1978, abandoned, which is a continuation of Ser. No. 746,373, Dec. 1, 1976, abandoned.

[30] Foreign Application Priority Data

Dec. 1, 1975 [CH] Switzerland .................. 15555/75
Sep. 23, 1976 [CH] Switzerland .................. 12074/76

[51] Int. Cl.³ .................................................. G01N 29/04
[52] U.S. Cl. .............................................. 73/626; 73/642
[58] Field of Search .................... 73/626, 641, 642; 128/2 V, 2.05 Z; 367/105

[56] References Cited

U.S. PATENT DOCUMENTS

| | | | |
|---|---|---|---|
| 3,693,415 | 9/1972 | Whittington | 73/679 |
| 3,881,164 | 4/1975 | Kossoff | 340/1 R |
| 3,918,024 | 11/1975 | Macovski | 340/1 R |
| 3,919,683 | 11/1975 | Itamura et al. | 73/67.8 S |
| 3,936,791 | 2/1976 | Kossoff | 73/626 |
| 4,005,382 | 1/1977 | Beaver | 340/1 R |
| 4,019,169 | 4/1977 | Takamizawa | 340/1 R |
| 4,119,938 | 10/1978 | Alais | 367/105 |
| 4,163,394 | 8/1979 | Soldner | 73/626 |

Primary Examiner—James J. Gill
Attorney, Agent, or Firm—Jon S. Saxe; Bernard S. Leon; Mark L. Hopkins

[57] ABSTRACT

A method for producing cross-sectional images using an ultrasonic imaging unit operating on the pulse-echo principle, which unit includes a transducer system having a stationary elongated array of adjacent transducer elements with transverse electrode segments adjacent one another on one side of the array. Successively and cyclically selected groups of adjacent elements are energized to produce an ultrasonic beam as a result of pulsed signals being applied to the corresponding electrode segments. Focussing of the ultrasonic beam produced by each group of the transducers is effected by having the transmitter signals applied to the electrode segments or subgroups thereof, and/or the echo-signals derived by the electrode segments from the reflected energy, time shifted relative to one another, in which each transmitter or echo-signal has a time shift associated thereto which is a function of the distance between the corresponding electrode segments (or subgroups of segments) and the center of the group of transducers.

33 Claims, 32 Drawing Figures

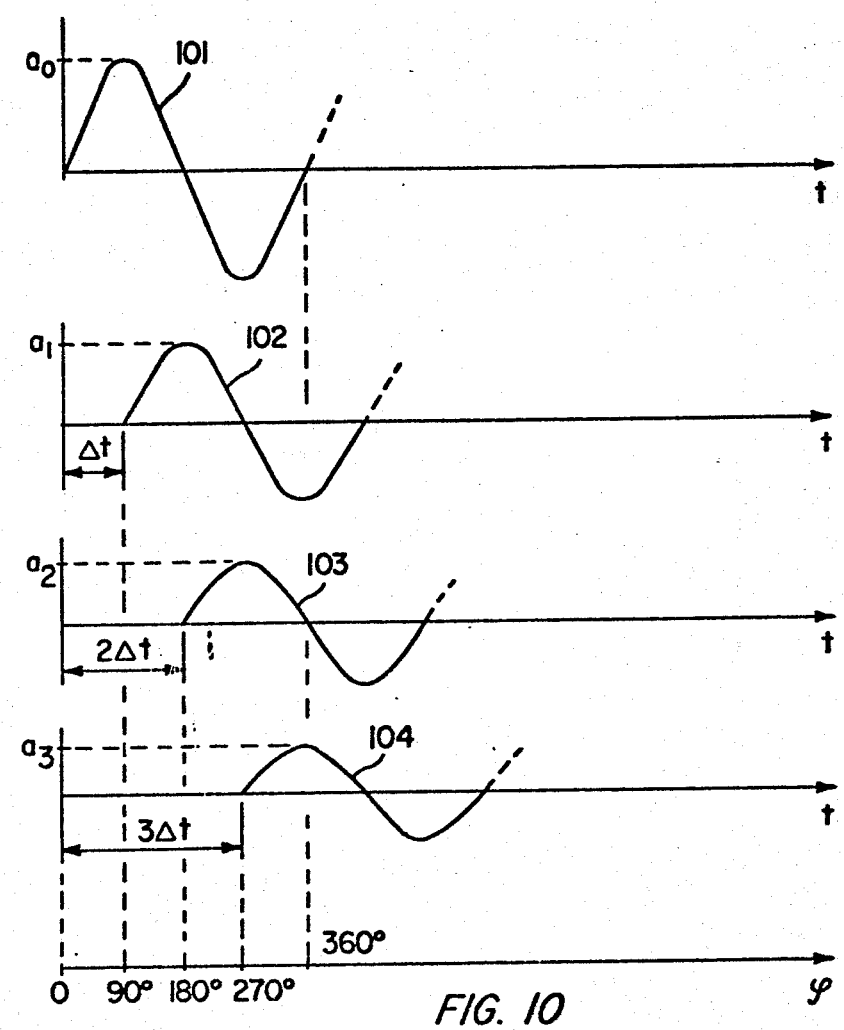
FIG. 10
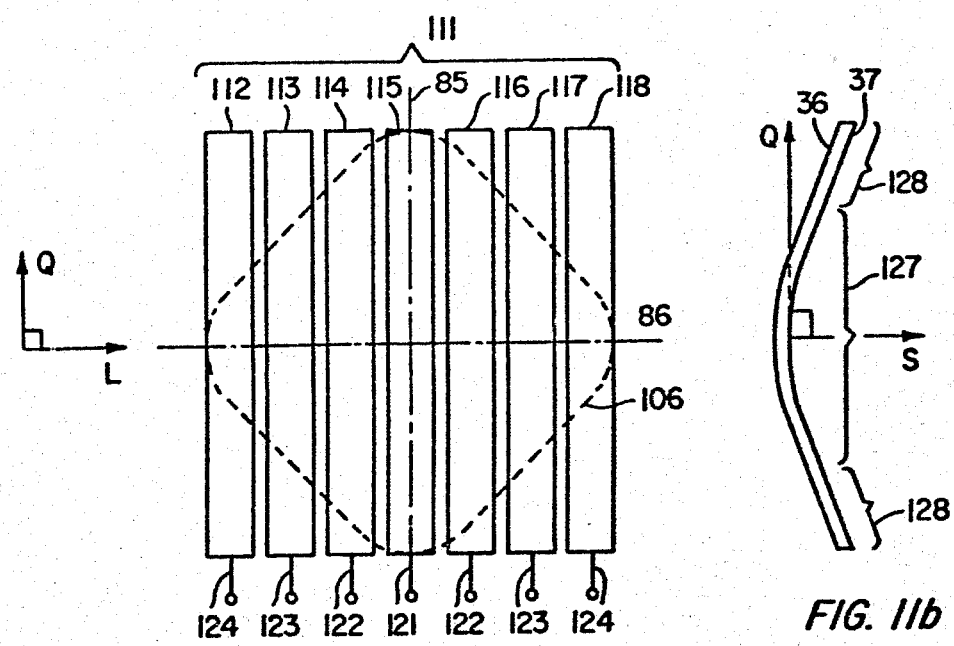
FIG. 11a
FIG. 11b

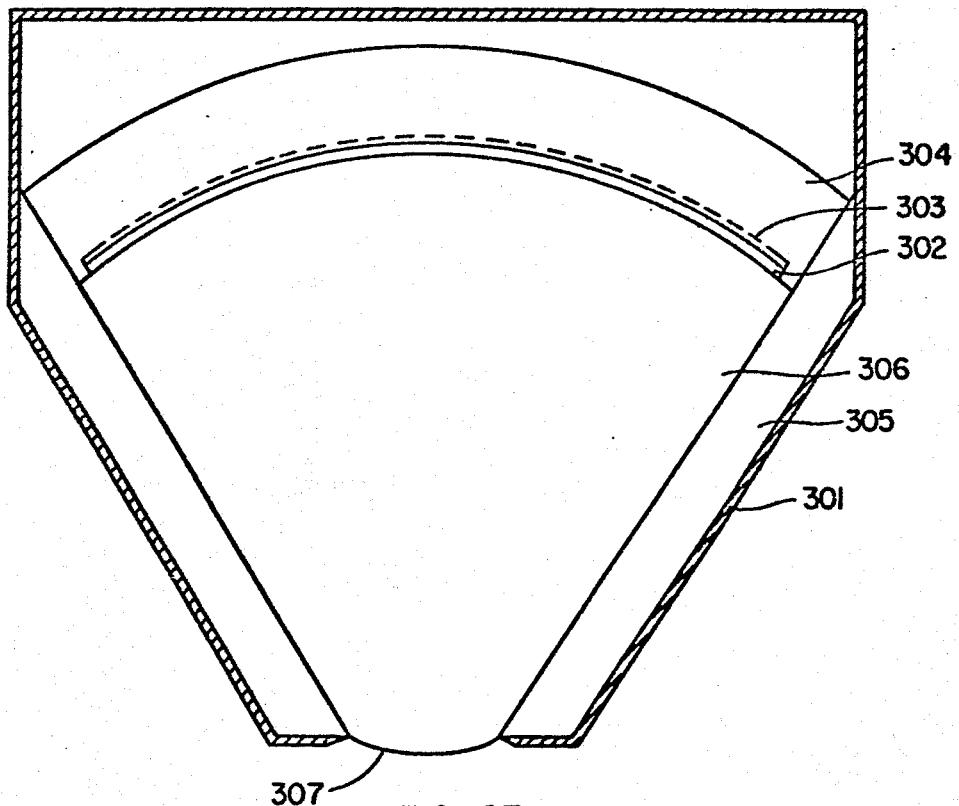
FIG. 23
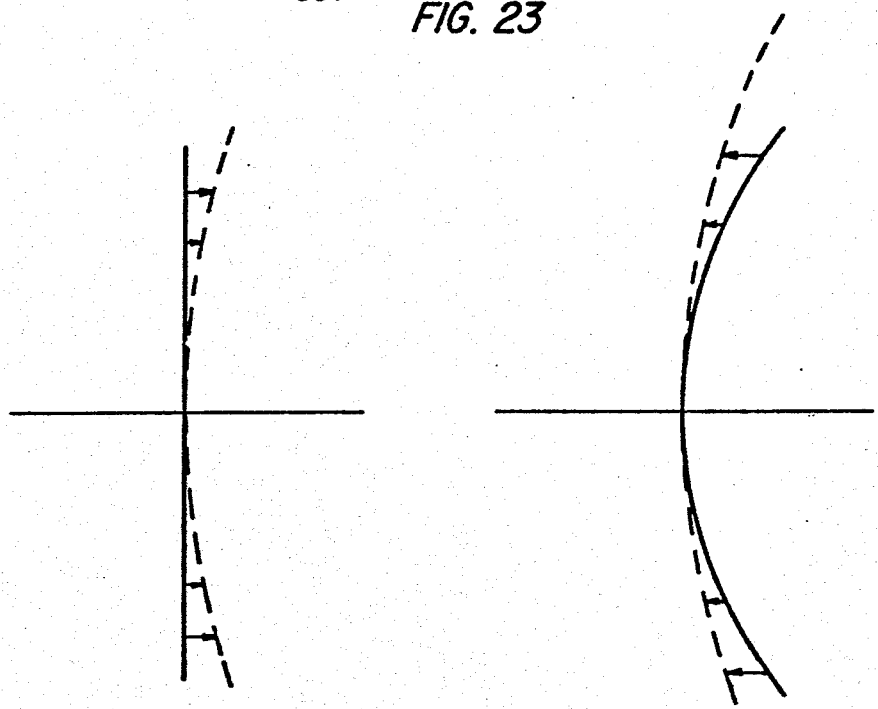
FIG. 24
FIG. 25

METHOD AND APPARATUS FOR PRODUCING CROSS-SECTIONAL IMAGES USING ULTRASOUND

This is a continuation of application Ser. No. 844,092 filed Mar. 6, 1978, which itself is a continuation of application Ser. No. 746,373 filed Dec. 1, 1976, both of which are abandoned.

BACKGROUND OF THE INVENTION

The invention relates to a method of producing cross-sectional images using an ultrasonic imaging unit operating on the pulse-echo principle and comprising a transducer system which includes a stationary elongated array of adjacent transducer elements and having transverse electrode segments having on at least one side transverse electrode segments adjacent one another. In the method, successively and cyclically selected groups of adjacent transducer elements of the transducer system are used to produce an ultrasonic beam in response to pulsed electrical transmitter signals applied to the electrode segments. The transducer elements are also used to transmit the ultrasonic beam into a heterogeneous body, receive echoes reflected from a discontinuity in the body, and generate an electric echo signal in response to the received echoes. The invention also relates to an ultrasonic imaging unit for performing the method.

In order to produce ultrasonic images (more particularly for producing cross-sectional images) it is conventional for an ultrasonic transducer to be mechanically moved. This has various disadvantages. If the transducer is moved by hand, the scanning process is lengthy and dependent on the skill of the operator. If the transducer is moved by a motor, a relatively heavy water bath is usually required. In addition, the extra distance travelled through the water bath results in a reduction in the maximum possible image frequency.

In order to obviate these disadvantages, therefore, ultrasonic imaging units with electronic scanning have been developed, the ultrasonic beam being linearly shifted in time.

In a known ultrasonic imaging unit of the aforementioned kind (U.S. Pat. No. 3,881,466), the transducer system produces an unfocussed ultrasonic beam and the transverse resolution is determined by the width of the transducer elements. In the known device, there is a limit to which the transverse resolution can be improved by reducing the width of the transducer elements, the limit being set by the minimum width of the ultrasonic beam. Although the cross-sectional images produced by the known device are relatively distinct, it has been found in practice that still higher transverse resolution is desirable for many applications.

SUMMARY OF THE INVENTION

An object of the invention, therefore, is to provide a method and an ultrasonic imaging unit which can give higher transverse resolution.

The method according to the invention is characterized in that, in order to focus the ultrasonic beam produced by each group of the transducers, the transmitter signals applied to the electrode segments or subgroups thereof and/or the echo signals given by the electrode segments or subgroups thereof are time-shifted with respect to one another, each transmitter or echo signal being associated with a time shift which is a function of the distance between the corresponding electrode segment or subgroup of segments and the center of the group of transducers.

The invention also relates to an ultrasonic imaging unit for performing the method according to the invention, the unit comprising a timing generator for producing a pulsed electric timing signal; a transducer system comprising a stationary elongated array of adjacent transducer elements and comprising transverse electrode segments adjacent one another on at least one side, the transducer system being used to produce an ultrasonic beam in response to pulsed transmitter signals derived from the electric timing signal, to transmit the ultrasonic beam into a heterogeneous body, to receive echoes reflected from a discontinuity in the body, and produce an electric echo signal in response to the received echoes; and an element-counter selector device connected to the timing generator, the transducer system and an indicator device and used for successively and cyclically selecting groups of adjacent elements of the transducer system, generating the ultrasonic beam, applying the transmitter signals to the electrode segments of the selected group, and transmitting the echo signals produced by the group to the indicator device, which is used to convert the echo signals into a visible image reproducing the cross-sectional structure of the heterogeneous body.

The ultrasonic imaging unit according to the invention is characterized by a transmitter-signal generator inserted between the timing generator and the element-counter selector device and used to derive transmitter signals for the electrode segments or a subgroup thereof of the selected group of transducers, the signals being time-shifted with respect to one another and obtained from the timing signals given by the timing generator.

The ultrasonic imaging unit is further characterized by an echo-signal receiver means inserted between the element-counter selector device and the indicator device and used to produce a relative time shift between the echo-signals delivered by the electrode segments or subgroup thereof of the group of transducers.

BRIEF DESCRIPTION OF THE DRAWINGS

Some embodiments of the invention will now be described with reference to the accompanying drawings, in which:

FIG. 9b is a cross-section showing the shape of the irradiating surface of the group of transducers in FIG. 9a.

FIG. 10 shows diagrams of the transmitter signals which according to the invention are applied to the electrode segments of the group of transducers according to FIG. 9a.

FIG. 11a is a rear view of a group of transducers having seven electrode segments used in another preferred embodiment of the ultrasonic imaging unit according to the invention.

FIG. 11b is a cross-section through a preferred shape of the irradiating surface of the group of transducers in FIG. 11a.

FIG. 12 shows diagrams of the transmitter signals which according to the invention are applied to the electrode segments of the group of transducers according to FIG. 11a.

FIG. 23 is a diagram of a sound head with an arcuate transducer system.

FIGS. 24 and 25 illustrate the production of a cylindrical wave front in two variants of the invention.

DESCRIPTION OF THE PREFERRED EMBODIMENT(S)

Figure 1:
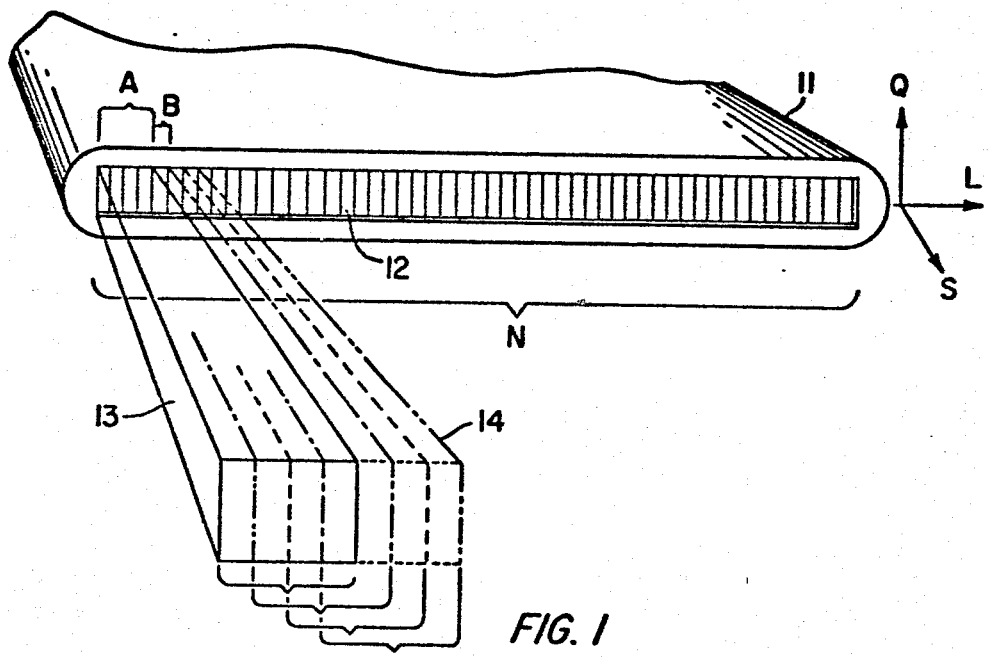
FIG. 1 is a perspective view of the transducer system in the previously-mentioned prior-art ultrasonic imaging unit.
Figure 2:
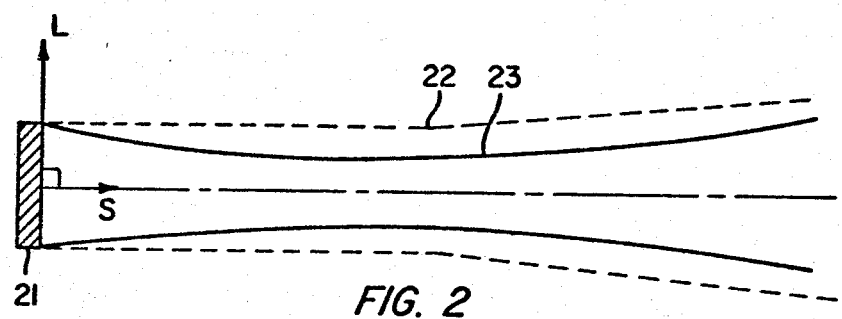
FIG. 2 is a diagrammatic cross-section of the radiation characteristic of a group of transducers according to the invention, compared with the radiation characteristics of a group of transducers in the system according to FIG. 1.

As FIG. 1 shows, the transducer system 11 of the known ultrasonic imaging units (e.g. U.S. Pat. No. 3,881,466) comprises a stationary elongated array of adjacent transducer elements 12. Groups of A adjacent elements 12 are successively stimulated to produce pulses. The location of each successive group of A elements is shifted the longitudinal distance of B elements from the position of the immediately preceding group. The ultrasonic beam 13 is thereby moved in the direction of arrow L, as shown, by the series of chain-dotted rectangles 14 showing the instantaneous position of beam 13 after equal intervals of time. Note that each group of transducers in the known transducer system 11 generates an unfocussed ultrasonic beam 13, since all the A elements in the group of transducers are simultaneously energized so as to yield pulses. The unfocussed radiation characteristic 22 of the ultrasonic beam 13 in FIG. 1 is shown in FIG. 2.

In FIG. 1, an orthogonal system of coordinates is defined by three arrows, Q, L and S. Arrow L is along the longitudinal axis of the irradiating surface of the transducer system 11. Arrow S is parallel to the major axis of the ultrasonic beam 13. Arrow Q is at right angle to the plane defined by arrows L and S. The positions of the cross-sections and elevations shown in the accompanying drawings are defined with respect to this coordinate system.

Figure 3:
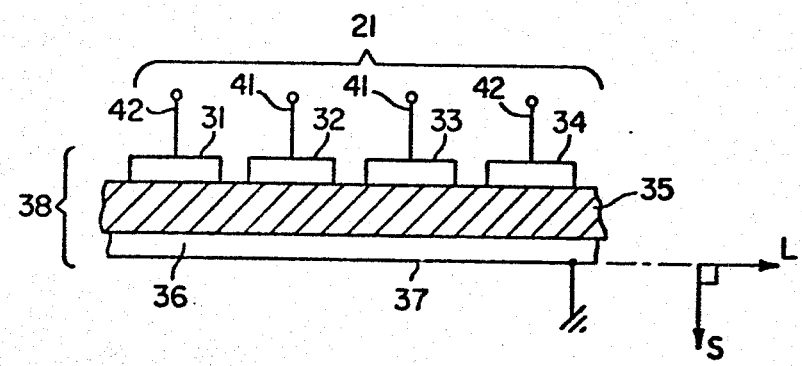
FIG. 3 is a diagrammatic cross-section through a preferred embodiment of an arrangement of transducers in the transducer system of FIG. 1.

FIG. 3 is a partial cross-section showing the structure of a preferred arrangement of transducers 38 for performing the method according to the invention. Arrangement 38 comprises a complete electrode 36 which is grounded and one surface 37 of which is used as an irradiating surface. Arrangement 38 further comprises a piezoelectric layer 35 and electrode segments 31–34, shown in rear view in FIG. 4.

It is clear from the preceding description of arrangement 38 that the transducer elements according to the invention can have common parts such as the piezoelectric layer 35 or the complete electrode 36. The arrangement 38 according to the invention can be operated simply by providing it with electrode segments on one side, which are supplied with the time-shifted transmitter signals and from which echo signals can be obtained. Thus, each electrode segment defines a transducer element according to the invention.

The effect obtained by the invention, i.e. higher transverse resolution, is mainly due to a novel manner of operation of the transducer system. This will be explained in detail, firstly with reference to FIGS. 2, 4 and 5.

Figure 4:
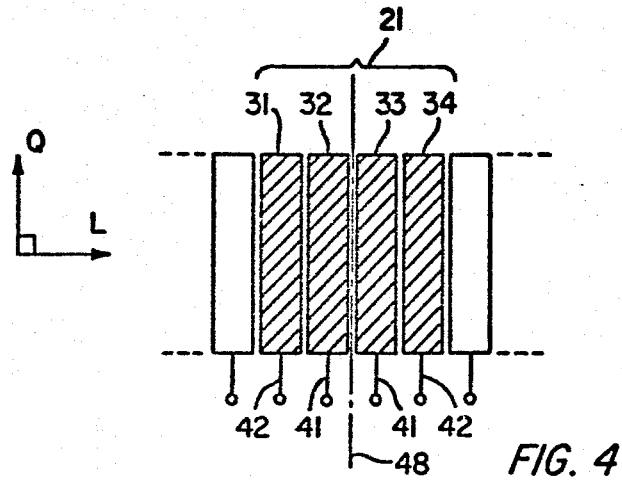
FIG. 4 is a rear view of a group of transducers according to the invention, comprising four transducer elements.
Figure 5:
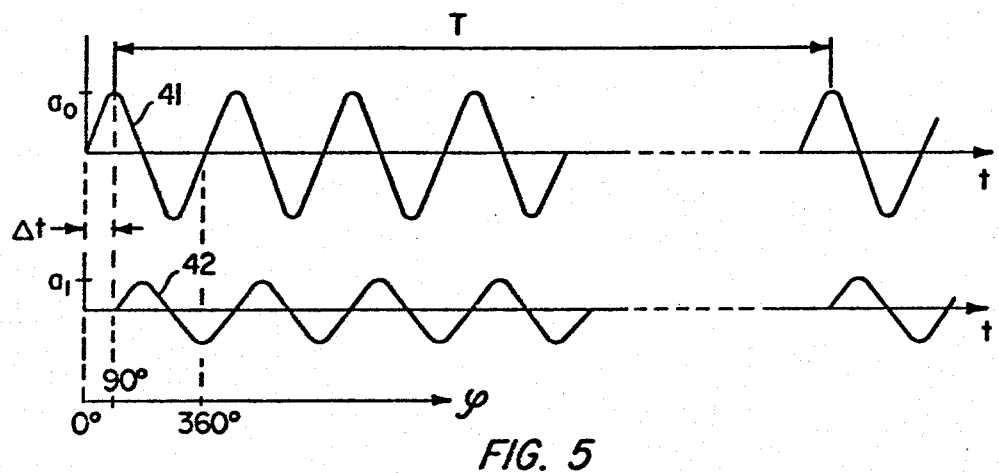
FIG. 5 illustrates graphically a pair of transmitter signals which, according to the invention, are applied to the electrode segments of the group of transducers in FIG. 3.

FIG. 4 shows electrode segments 31–34 of a group of transducers 21 according to the invention. In order to produce an ultrasonic beam according to the invention, transmitter signals 41, 42 which are time-shifted relative to one another as shown in FIG. 5 are applied to the electrode segments 31–34, the transmitter signals for the outer segments 31, 34 having a phase lead. In this manner a weakly focussed ultrasonic beam 23 is produced (FIG. 2).

In a preferred embodiment of the invention, a time shift is produced not only between the transmitter signals but also between the echo signals received by the individual elements of the group of transducers. The group of transducers 21 shown in FIG. 4 has four elements for transmitting and receiving, the transmitted signals and the time-shifted echo signals of the outer elements having a phase lead of 90°. According to the invention, the phase lead is defined with respect to a period (360°) of the high-frequency carrier signal (e.g. 2 MHz), which is supplied to the electrode segments of the successive groups of transducers in pulses at a repetition frequency of e.g. 2 KHz and at a suitable phase angle.

The effect of operating group 21 according to the invention can be improved by the following additional measures:

(1) It has been found advantageous to select the following combinations of phase lead for the outer elements of the group:

|  | Transmitter signals | Echo signals |
|---|---|---|
| either approx. | 90° | approx. 45° |
| or approx | 45° | approx. 90° |

As a result of these different values of the phase lead for the transmitter and echo signals, the radiation characteristic 23 according to the invention (FIG. 2) is additionally narrowed over a certain depth.

(2) Advantageously, the transmitter and echo signals are weighted. As shown in FIG. 5, the inner electrode segments 32, 33 are supplied with a transmitter signal having a higher amplitude $a_o$. Similarly, the echo signals received from the inner segments are multiplied by a higher weighting factor than the echo signals from the outer elements.

Advantageously, the weighting ratio is 2:1 for both the transmitter and the echo signals.

Figure 6:
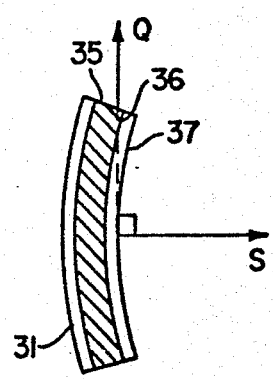
FIG. 6 is a diagrammatic cross-section parallel to the QS plane in FIG. 1 of an irradiating surface in the arrangement of FIG. 3, the surface having a suitable shape for weakly focussing the ultrasonic beam in the QS plane.

(3) Advantageously, weak focussing is also produced in the Q direction in FIG. 1, e.g. by using a transducer arrangement comprising a slightly curved irradiating surface 37 (see e.g. FIG. 6).

Figure 7:
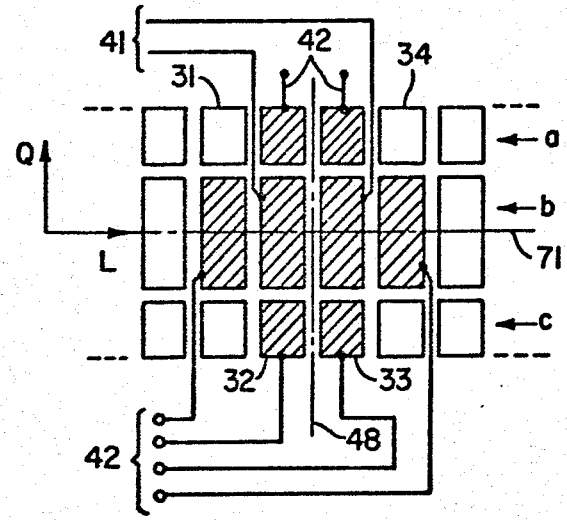
FIG. 7 is a rear view of an embodiment of the arrangement of FIG. 3 whereby the weak focussing in the QS plane is obtained by means of a flat irradiating surface instead of the concave surface in FIG. 6.

The weak focussing in the Q direction can also be electronically produced, using a transducer arrangement as in FIG. 7, in which each of the electrode segments is divided into three parts a, b, c in the Q direction. As shown in FIG. 7, only the shaded parts of the electrode segments are used for transmitting or receiving. The inner parts 32b and 33b are energized with the transmitter signal 41 and the remaining active parts are energized with the transmitter signal 42. The resulting system is electronically more complicated than the transducer arrangement comprising a curved irradiation surface, but it only requires a transducer arrangement having a flat irradiation surface, which is cheaper.

In the known transducer system 11 in FIG. 1, the ultrasonic beam 13 can be displaced by the width of a transducer element 12 after each transmitting and reception period. However, the number of lines in the image and the resolution can be increased if the ultrasonic beam is displaced by a smaller amount each time, e.g. by half the width of an element. The same result, of course, can be obtained by halving the width of the element, but the result is to double the number of elements and correspondingly increase the complexity.

Figure 8A:
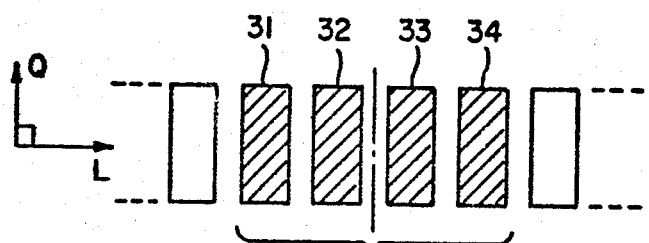
FIGS. 8a–8c shows an advantageous configuration of groups of transducers which are cyclically and successively selected.
Figure 8B:
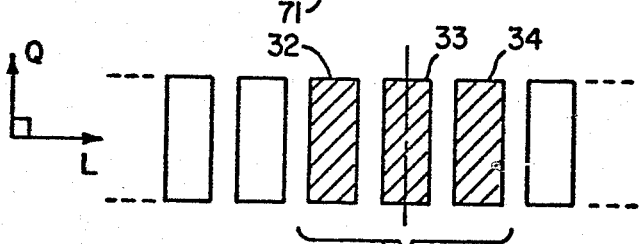
Figure 8C:
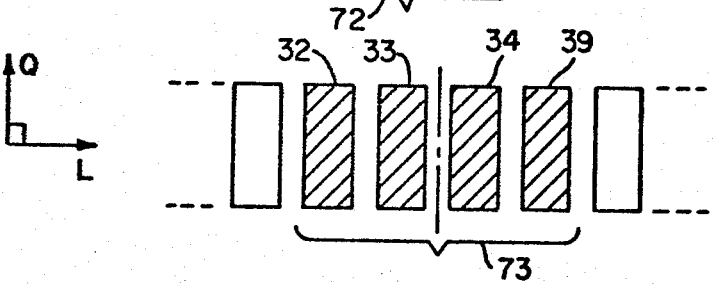

In a preferred embodiment of the invention (FIGS. 8a, 8b and 8c) the ultrasonic beam is displaced by half the width of an element in that successively selected groups of transducers 71, 72, 73 alternately contain an even and an odd number of elements, the successive groups being alternately formed by reducing the number of segments in one direction and increasing the number of segments in the opposite direction. The amplitudes and phases of the transmitter signals or the time-shifted echo signals are selected so that the shape of the ultrasonic beam remains substantially uniform, independently of the number of elements in the group of transducers. The following relations of amplitudes and phase give very similar beam shapes, e.g. when four and three elements are used alternately:

| With four elements: | Element | 31 | 32 | 33 | 34 |
|---|---|---|---|---|---|
| Transmission | Amplitude | 0.5 | 1 | 1 | 0.5 |
|  | Phase | 90° | 0° | 0° | 90° |
| Reception | Amplitude | 0.5 | 1 | 1 | 0.5 |
|  | Phase | 45° | 0° | 0° | 45° |
| With three elements: | Element |  | 32 | 33 | 34 |
| Transmission | Amplitude |  | 1 | 1 | 1 |
|  | Phase |  | 45° | 0° | 45° |
| Reception | Amplitude |  | 1 | 1 | 1 |
|  | Phase |  | 22.5° | 0° | 22.5° |

Figure 9A:
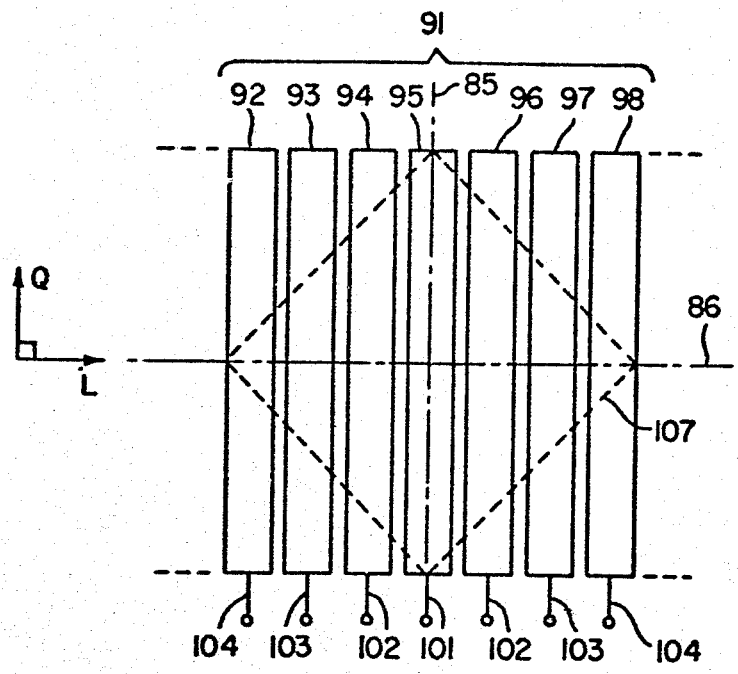
FIG. 9a is a rear view of a group of transducers according to the invention comprising seven electrode segments and used in a second embodiment of the ultrasonic imaging unit according to the invention.
Figure 9B:
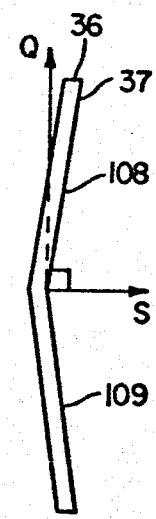
Figure 16:
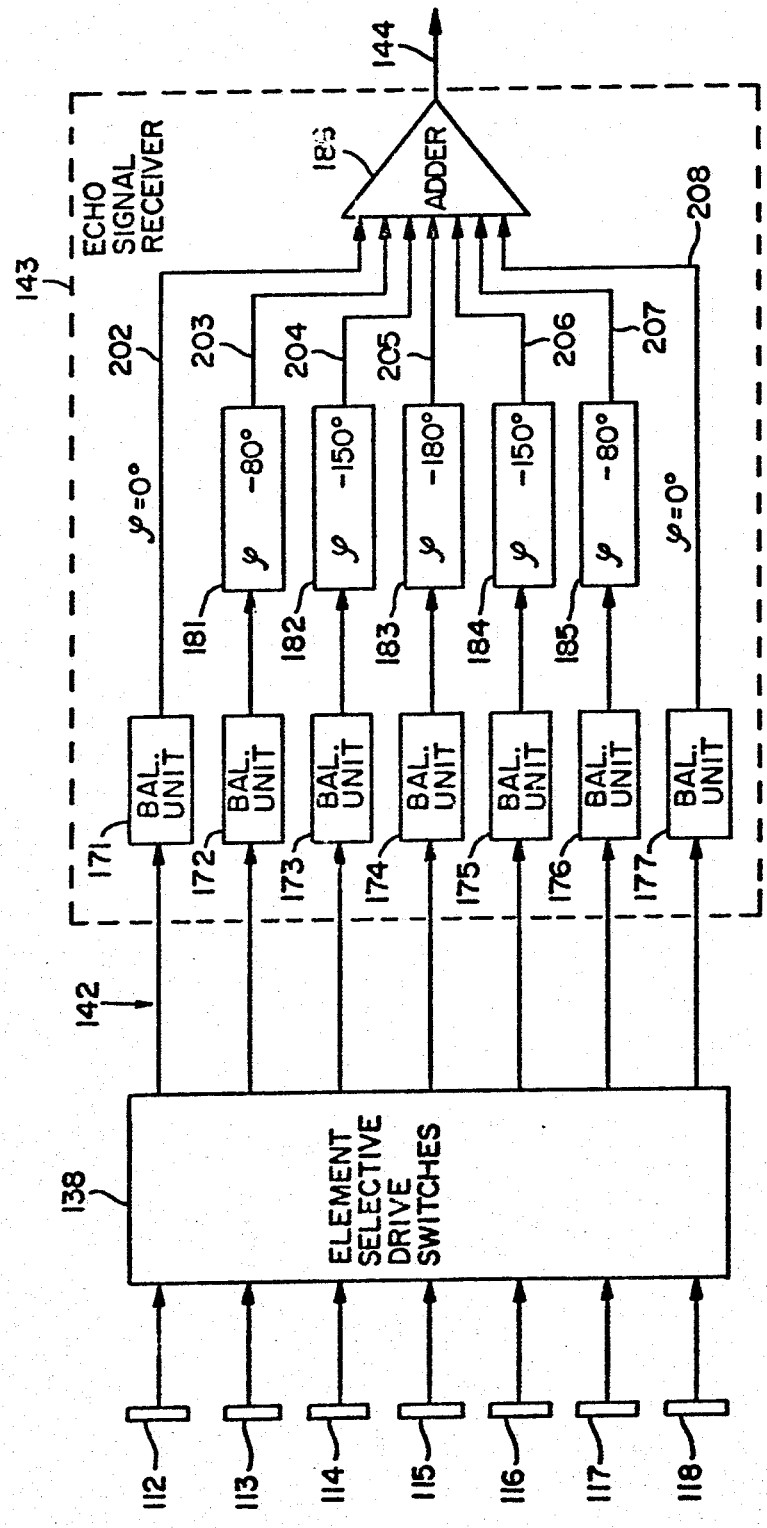
FIG. 16 is a block diagram illustrating the echo-signal receiver in the device of FIG. 13.

A second embodiment of the invention will be described initially with respect to FIGS. 9a, 9b and 10. It is known (Swiss Pat. No. 543,313) that the ultrasonic beam can be efficiently focussed over a considerable depth if an ultrasonic wave having a conical wave front is radiated. A wave front of this kind is radiated e.g. by a conical ultrasonic transducer. According to the invention, a conical irradiation surface can be approximated if the phase angle $\phi$ is made to increase in linear manner with the distance between the transducer elements 92–98 and the center of the group of transducers, in the case of the transmitter signals 101–104 in FIG. 9a for the time-shifted echo signals 202–208 (FIG. 16). FIG. 10 shows the linear increase in the phase angle $\phi$. A linear increase in the phase angle of the reflected ultrasonic waves is also obtained in the Q direction by shaping the irradiating surface 37 as shown in cross-section in FIG. 9b. The dashed line 107 in FIG. 9a shows the position of constant phase on the irradiation surface of the transducer system; for simplicity, the drawing shows a phase which varies continuously in the L direction, instead of varying stepwise as in the present example. In the present example of the locus of constant phase is a set of straight lines 107, instead of being a circle as in the case of a conical wave front.

Figure 12:
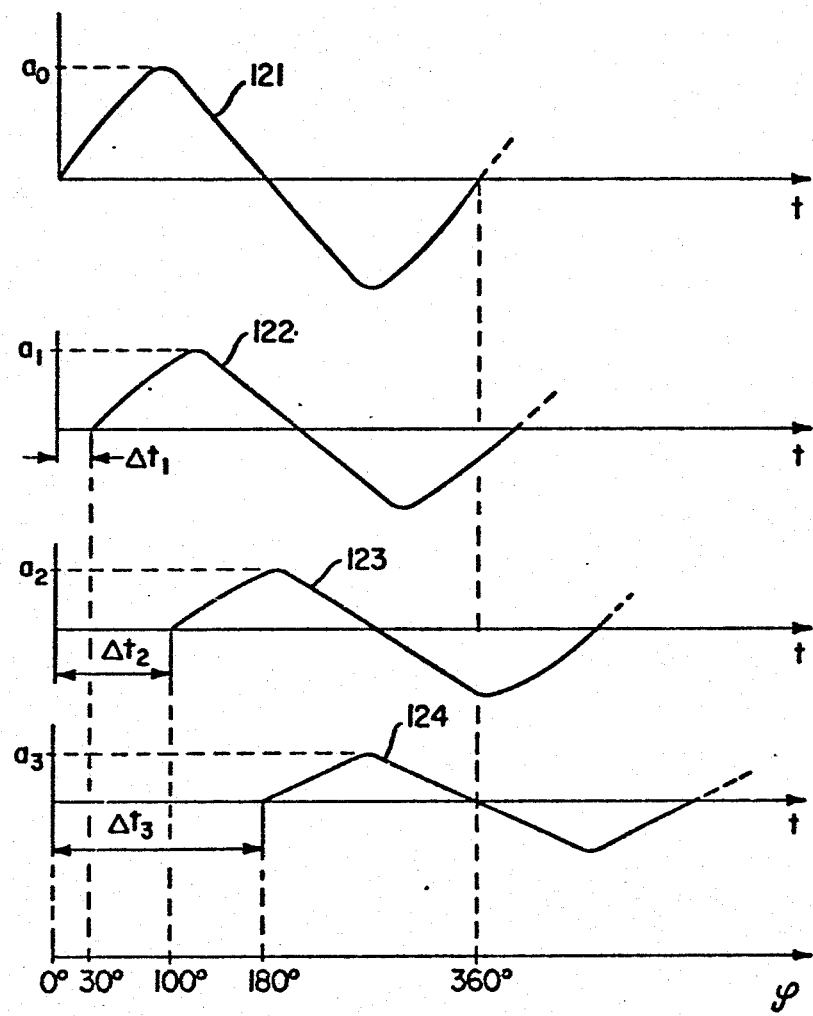

A better approximation of a conical wave front can be obtained by the embodiment of the invention illustrated initially with respect to FIGS. 11a, 11b and 12. In this embodiment, the phase angle of the transmitter signals or time-shifted echo signals is a quadratic function of the position of the corresponding elements in the center of the group of transducers, and is a linear function at the edge. A corresponding phase angle distribution in the Q direction is obtained by shaping the irradiating surface 34 as shown in FIG. 11b with respect to a cross-section of the transducer system. Surface 37 in FIG. 11b defines preferably a hyperbola. A curve of this kind is circular in the central region 127 and linear at the edge. The improvement obtained with this embodiment is shown by the fact that the locus of constant phase 106 shown in FIG. 11a has rounded corners.

Note that the radiating groups of transducers in the embodiments in FIGS. 9a, 11a have a greater area than in the embodiment in FIG. 4. This greater area results in a correspondingly greater pressure, which is required for obtaining better resolution.

Advantageously in the last-mentioned embodiments, as in the others, the inner part of the radiating group of transducers transmits at a higher amplitude and the echo signals received there are multiplied by a higher weighting coefficient on reception, thus improving the short-range field.

The dimensioning of groups 21 and elements 31–34 as in FIG. 4 for obtaining a weakly focussed ultrasonic beam 23 as in FIG. 2 will be explained initially with respect to FIGS. 18 and 19. An efficient weakly-focussing group of transducers is characterized in that its width W and length L is 15–30 wavelengths. The radius of curvature R (FIG. 19) of the wave front is made approximately equal to half the depth of the examined body, and is preferably somewhat smaller. In the case of a group of transducers comprising four elements, the width of the individual elements is made such that the phase difference between the waves radiated by neighboring elements is not appreciably greater than 90°. If these values of the radius of curvature and the phase difference are exceeded, there is a corresponding impairment in the shape of the beam and consequently in the transverse resolution. However, weak focussing according to the invention can be obtained, at least in principle, with a phase difference between 30° and 180°.

Figure 18:
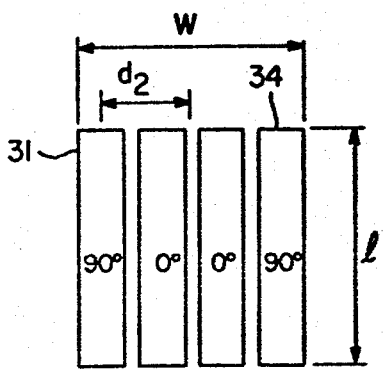
FIGS. 18 and 19 illustrate the dimensioning of a group of transducers according to the invention and the elements thereof.
Figure 19:
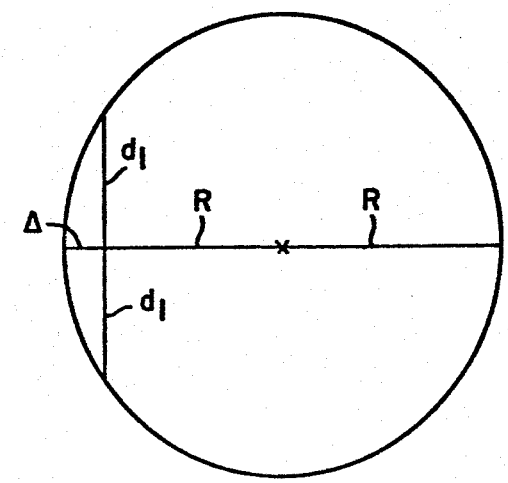

The dimensions of the transducer elements will now be illustrated with respect to a specific example (FIGS. 18 and 19). As shown in FIG. 18, the two inner elements in the group transmit at phase 0° and the two outer elements at phase 90°. From FIG. 19 and by the chord theorem, there is obtained $$d_1^2 = 2R \cdot \Delta \quad (1)$$

in which
$d_1$ = the lateral shift leading to the desired phase shift of 90°.
R = radius of curvature of the wave front, and
$\Delta$ = the distance corresponding to a phase shift of 90°.
In the present case $$\Delta = \lambda/4 \quad (2)$$

with $\lambda$ = wavelength.

If R is made equal to 80 mm (approximately half the depth of the examined body) and $\lambda = 0.75$ mm (this wavelength corresponds to a frequency of 2 MHz), we obtain $d_1 = 5.48$ mm. If the element is at a distance $d_2 = 6$ mm from the center of the group of transducers this value of $d_2$ is approximately equal to the previously-calculated distance $d_1$.

Figure 13:
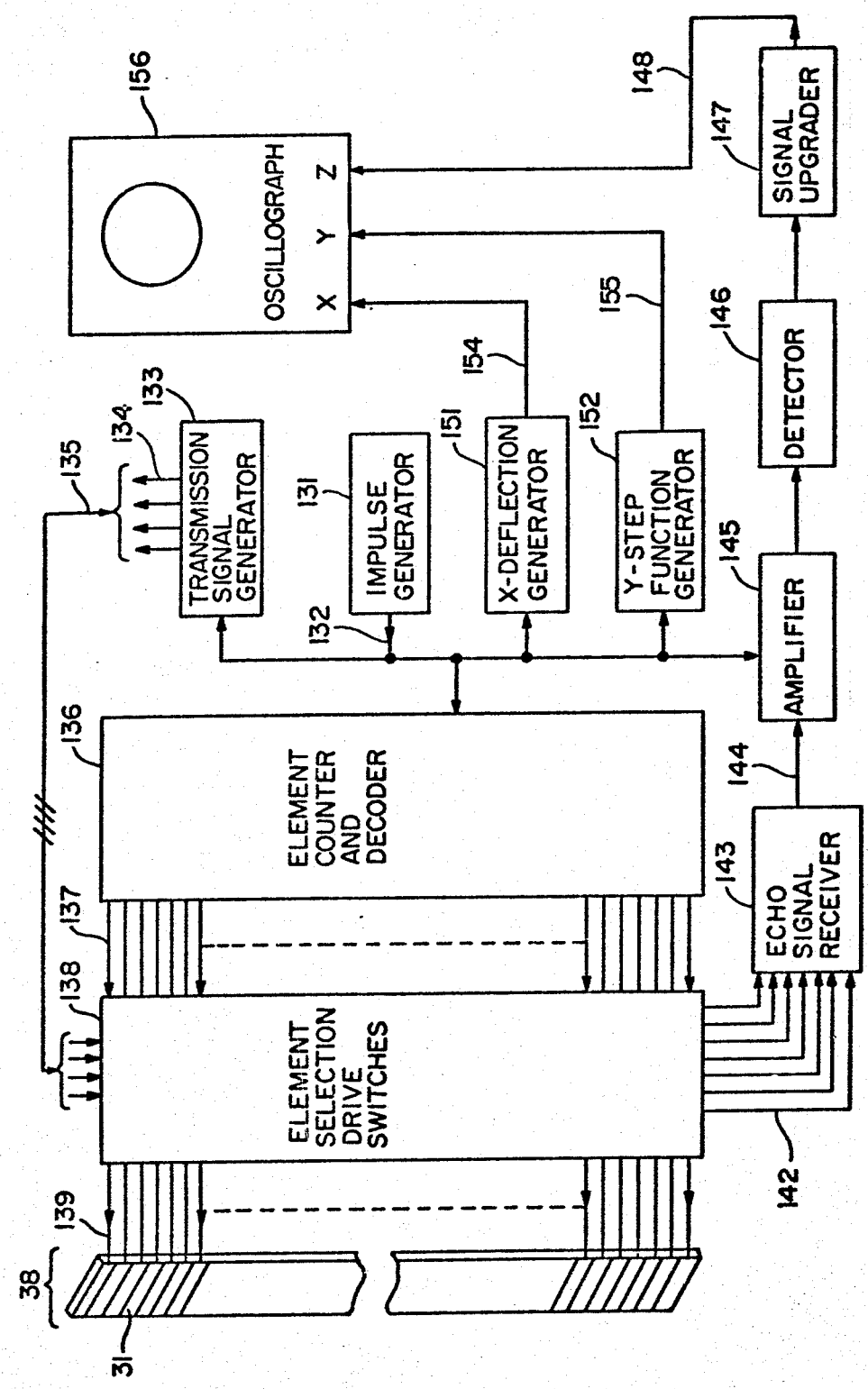
FIG. 13 is a schematic block diagram illustrating a preferred embodiment of the ultrasonic imaging unit according to the invention.

FIG. 13 is a block circuit diagram of an ultrasonic imaging unit according to the invention which, as shown in FIG. 11a uses seven-element groups of transducers for transmission and reception. The block circuit diagram of FIG. 13 shows a transducer arrangement 38 as in FIG. 3, a timing generator 131, a timing signal 132 delivered by generator 131, a transmitter-signal generator 133, transmitter signals 134 supplied by generator 133 over lines 135 to element-selector drive switches 138, an element counter and decoder 136 for controlling switches 138 and connected to timing generator 131, echo signals 142 delivered by a group of transducers, an echo signal receiver 143, the combined echo signal 144 at the output of receiver 143, a time-sensitive amplifier 145, a detector 146, a signal processor 147, the output signal 148 of processor 147, an X-deflection generator 151, a deflection signal 154 given by generator 151, a Y-stage function generator 152, a stage function signal delivered by generator 152, and a reception oscillograph 156 having three inputs X, Y and Z.

The timing generator 131 generates periodic timing pulses 132 triggering the transmission of an ultrasonic signal and the generation of the necessary sync signals. Four electric transmitter pulses 121–124 (see FIG. 14) are generated in the transmitter signal generator 133. Three of the signals 122, 123, 124 have a phase lead corresponding to a carrier-signal phase of +30°, +100° and +180° compared with a signal 121, whose phase is denoted by 0°. These transmitter signals are supplied on lines 134. In unit 138 (the element selector drive switch arrangement) the transmitter signals are supplied to seven supply lines 139, on which the transmitter signals have the phase +180°, +100°, +30°, 0°, +30°, +100°, +180°. The element counter and decoder 136 switches the desired seven elements, either for transmission or for reception, via switch arrangement 138. After each pulse, the configuration in FIG. 11a is shifted by one element in the L direction. At the same time, the transmitter signals are cyclically interchanged with the different phases on the supply lines so that each element obtains the corresponding transmitter signal having the correct phase.

The echo signals 142 travel from the seven switched-on elements to the echo-signal receiver 143, where the signals are variously delayed, multiplied by various weighting factors, and then added. The output signal 144 of receiver 143 travels through a time-sensitive amplifier 145, which compensates the attenuation of the body tissue. The signal is then rectified in detector 146 and travels via processor 147 to the Z input of the reproduction oscillograph 156. Processor 147 compresses the dynamic range of the signal delivered by detector 146.

The X-deflection generator 151 generates a voltage which is proportional to the time which has elapsed since the last pulse was transmitted. The Y-stage function generator 152 generates a voltage proportional to the position of the central axis of the switched-on group of transducers.

Figure 14:
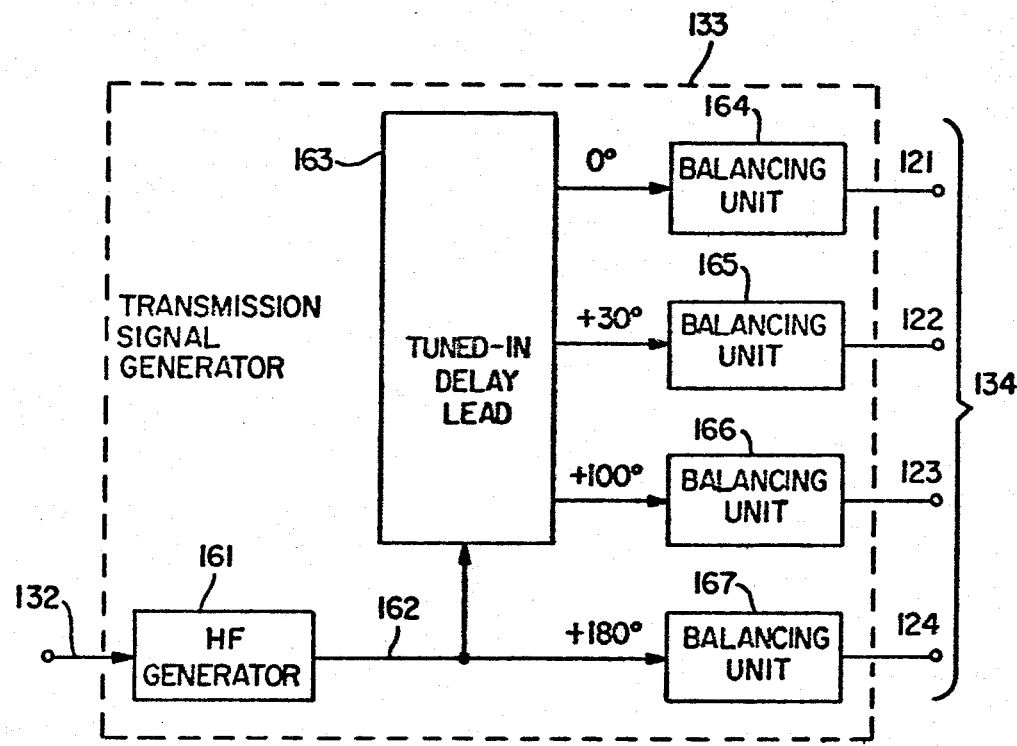
FIG. 14 is a block diagram illustrating the transmitter-signal generator in the device of FIG. 13.
Figure 15:
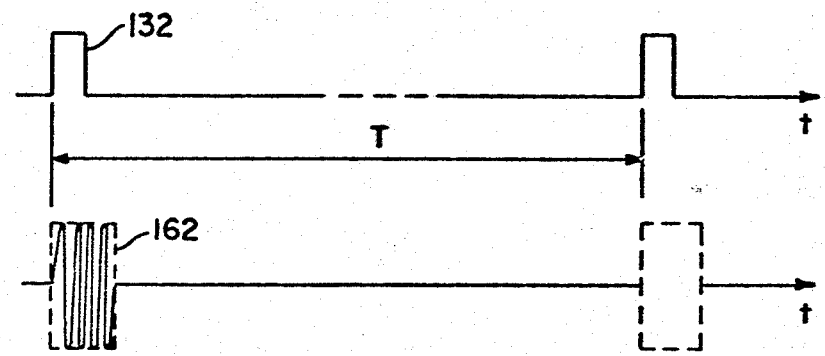
FIG. 15 shows diagrams of the timing pulse generated by the timing generator (FIG. 13) and of the pulsed sine wave derived from the timing pulse.

The construction and operation of the transmitter-signal generator 133 will be described initially with respect to FIGS. 14 and 15. The timing pulse 132 triggers a pulsed high-frequency generator 161 whose output signal 162 (a pulsed carrier signal) is delayed in the tapped delay line 163 so as to produce four signals having the phases 0°, 30°, 100° and 180°. In weighting units 164–167 these signals are multiplied by the corresponding weighting factors.

FIG. 16 shows the echo-receiver 143 in detail. The echo signals 142 are multiplied by the corresponding weighting factors in weighting units 171–177. They are delayed by phase shifters 181–185 and added in an adder 186.

Figure 17:
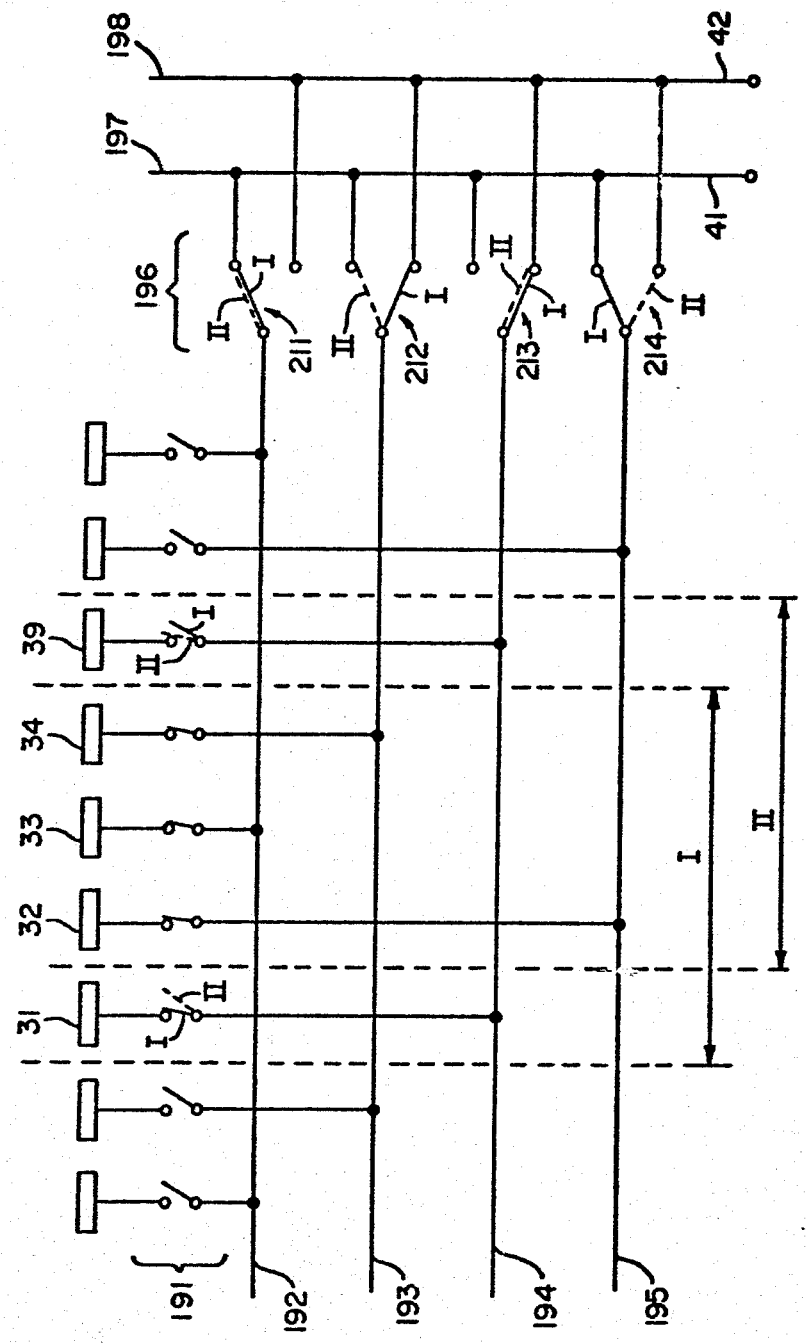
FIG. 17 illustrates the principle of a preferred embodiment of the element selector drive switch in the device of FIG. 13. For simplicity, the principle is illustrated in the case of a group of transducers containing only four elements, although the unit of FIG. 13 comprises groups each containing seven elements.

The basic principle of a preferred embodiment of the element selector drive switch 138 in the unit in FIG. 13 will be initially explained with respect to FIG. 17. For simplicity, the principle is explained in the case of a group of transducers containing only four elements, although the unit in FIG. 13 uses seven-element groups. The switching diagram shown in FIG. 17 can be used for triggering and shifting a group of four transducer elements. The two inner elements of each group (e.g. 32 and 33 in group I) are triggered with the transmitter signal 41 as in FIG. 5 and the two outer elements (e.g. 31 and 34 in group I) are triggered with the transmitter signal 42 in FIG. 5. In FIG. 17, the transducer elements are represented by the corresponding electrode segments 31, 32, 33, etc. By means of a switch system 191, the transducer elements are cyclically connected to four supply lines 192–195. These four lines are connected via a switch system 196 to two supply lines 197, 198, which are supplied with the transmitter signals 41, 42 having the amplitudes and phases shown in FIG. 5. FIG. 17 shows switch positions for two successive groups of transducers I (continuous lines) and II (dashed lines). The means of controlling the switch system 191 is self explanatory. In the switch system 196, in order to actuate a new group II, each switch (e.g. 213) is placed in the same position as the position previously occupied by the upper switch (e.g. 212) for actuating the preceding group I. The uppermost switch 211 takes the position previously occupied by the lowest switch 214. The same switches can be used for transmission and reception, if the electronic design of the switch system is suitable. If different electronic switches are required for transmitting and reception, the circuit in FIG. 17 can be duplicated, using separate supply lines for transmission and reception.

The advantages of the invention can be illustrated as follows:

The method according to the invention makes possible to attain higher transverse resolution, so as to obtain more distinct ultrasonic images.

In addition, the unit according to the invention is economic, since its expense is relatively low.

Owing to the weighting of the transmitter and echo signals according to the invention, there is an appreciable reduction in the secondary lobes of the radiation characteristic of an ultrasonic beam generated by a group of transducers according to the invention.

In addition, the embodiments of the invention described hereinbefore with respect to FIGS. 9a–12 produce ultrasonic beams having an approximately conical wave front, so that the ultrasonic beam is strongly focussed over a great depth.

Other advantages and properties of the invention are clear from the previous description of preferred embodiments.

The following description relates to variants of the invention for rotating the beam and thereby scanning in sectors.

Figure 20:
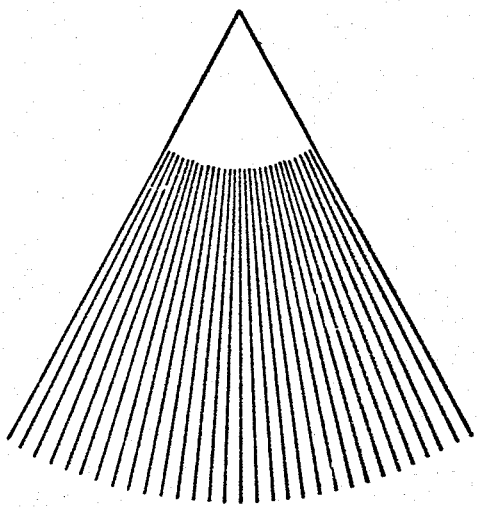
FIG. 20 is a diagram of the region which can be scanned by a sector-scan.
Figure 21:
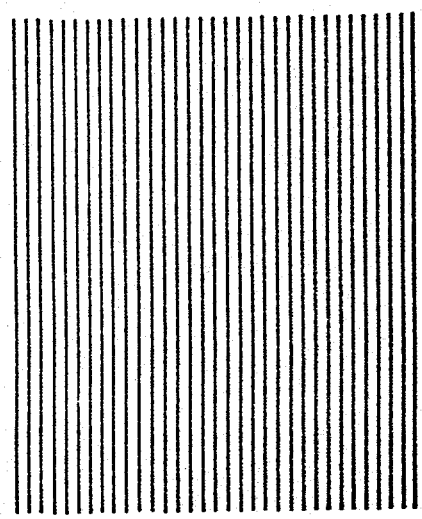
FIG. 21 is a diagram of the region which can be scanned by linear beam displacement.

In cardiology, for example, ultrasonic imaging in which the beam is rotated (FIG. 20) appears to yield better results than when the beam is moved in linear manner (FIG. 21). The reason is the small acoustic window through which the image has to be obtained. It is limited by the sternum and lungs and measures approximately 2×7 cm. In addition, the ribs make it difficult to obtain an image of the heart. A sector scanner requires an aperture of only a few square cm and is therefore the most suitable, whereas a linear scanner is usually over 10 cm in length and is inefficiently used.

Known sector scanners operate either on the "phased array" principle (J. Kisslo, OT. v Ramm, F. L. Thurstone, "A phased array ultrasound system for cardiac imaging". Proceedings of the Second European Congress on Ultrasonics in Medicine, Munich, 12–16 May 1975, pp. 67–74, edited by E. Kazner, M. deVlieger, H. R. Müller, V. R. McCready, Excerpta Medica Amsterdam-Oxford 1975), or are mechanical contact scanners (cf A. Shaw, J. S. Paton, N. L. Gregory, D. J. Wheatey, "A real time 2-dimensional ultrasonic scanner for clinical use". Ultrasonics, January 1976, pp. 35–40). The following description relates to an arc scanner which operates on the same principle as a linear scanner and has the scanning range of a sector scanner.

Figure 22:
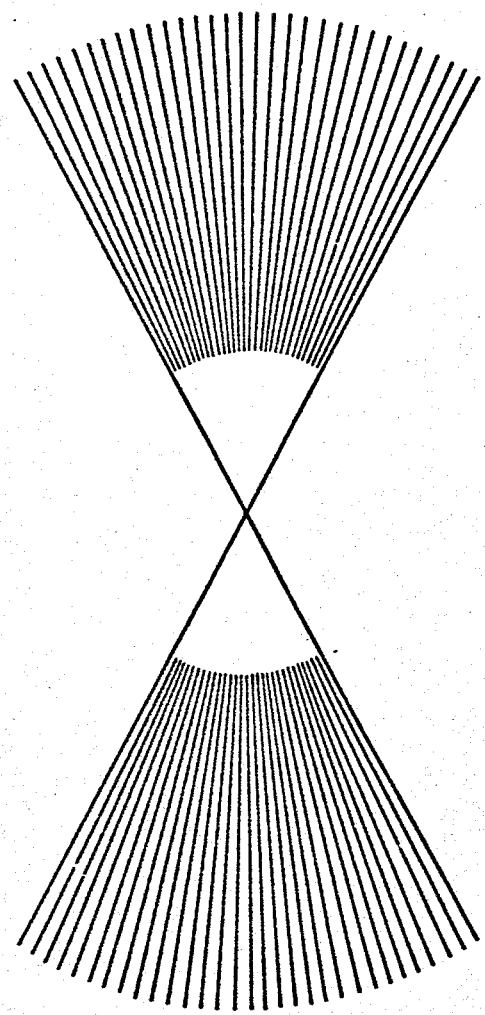
FIG. 22 is a diagram of the region which can be scanned with an arcuate transducer system (not particularly shown).

The main component of the arc scanner is a linear "array", the segments of which are disposed not on a straight line but on an arc. The scannable region is shown in FIG. 22. As in FIGS. 20 and 21, the transducer should be assumed to be above in the drawing. If the top half of the range is used as anticipatory path region and only the bottom half for imaging, a system with beam rotation is obtained as in FIG. 20. The complete sound head of an electronic arc scanner is shown in FIG. 23. An arcuate piezoceramic transducer 302 is disposed in the upper part of housing 301 and individual electrodes 303 are disposed at its top. Upwardly reflected ultrasound is absorbed in absorber 304. The lower part of the housing is lined with sound-absorbing material 305 and filled with an ultrasound-transmitting medium 306. At the bottom, the sound head is closed by a diaphragm 307. The diaphragm is at the center of the arc formed by the transducer, i.e. at the narrowest place in the scanable region (see FIG. 22). In order to eliminate interfering multiple reflections between the diaphragm and transducer from the image, the transit time between the transducer and diaphragm should be exactly the same as between the diaphragm and the most remote object which has to be imaged. If water is used for the anticipatory path, this means that the radius of the transducer arc must be exactly equal to the maximum depth of penetration, since the human body and water have approximately the same speed of sound (approx. 1500 m/sec.).

The shape of the beam can be optimized in a manner very similar to linear scanning, as described hereinbefore. If all segments of a group of transducers are operated and simultaneously switched on at the same phase, the second beam is focussed at the center of the arc, i.e. at the diaphragm. When the depth of penetration increases the beam becomes progressively wider, so that the lateral resolution of the system becomes progressively worse. A considerable improvement can be obtained if the focus is not at the center of the arc but at a point located at about approximately ⅔ of the maximum imaging depth measured from membrane 307. This is achieved by suitable phase-shifting of the individual transducer elements during transmission and reception. The phase shifting here has the opposite sign (phase lag) as in the linear scanner described previously.

The reason for this is explained in FIGS. 24 and 25 in the case of the transmitter. In the linear scanner (FIG. 24) an originally flat wave front (continuous line) is converted into a cylindrical front (dashed line). At increasing distances from the beam axis, the signal needs a correspondingly large phase lead. In the case of the arc scanner (FIG. 25), on the other hand, a strongly curved wave front (continuous line) is converted into a slightly curved front (dashed line). Thus, at increasing distances from the axis, the signal requires a progressively greater lag. Similar considerations apply to reception. Depending on the special dimensions of the group of transducers, the shape of the beam may be further improved by apodisation, e.g. by attenuating the amplitudes of the outer elements during transmission and reception. More particularly, the number of different phases used for focussing is critical.

Previously, only the shaping of the beam in the scanning direction has been discussed. However, weak focussing in the direction at right angles thereto may also be advantageous. Advantageously, the focal point is at the same place as in the first direction, i.e. at ⅔ of the maximum imaging depth. Focussing is obtained either by means of a suitable curved transducer or an acoustic lens disposed in front of the transducer. Of course, focussing can be electronically produced in this direction also, as in the previously-described linear scanner, if the greater complexity of the system is allowed for. Numerical calculations indicate that additional apodisation does not provide any further improvement of the shape of the beam. Apodisation is, however, advantageous if there is no focussing in the second direction which may be desirable for simplifying the construction. Apodisation can be obtained e.g. by means of segments which become progressively narrower outwards (see FIG. 28).

Electronically, the arc scanner has all the advantages of the linear scanner. Its disadvantage is that it requires a water anticipatory path, with the result that the sound head is heavy and awkward to handle and the maximum image frequency is only half that of a scanner without the anticipatory path. The anticipatory path, and therefore the sound head, can be reduced if water is replaced by a substance in which the speed of sound is lower than in water. In many organic liquids, and also in many silicone rubbers, the speed of sound is about 1000 m/sec. This means that the anticipatory path can be reduced by ⅓ and the volume of the sound head can be reduced by at least half, but the reflection is amplified and the sound beam is refracted at the interface between the anticipatory path region and the body tissue.

Figure 26:
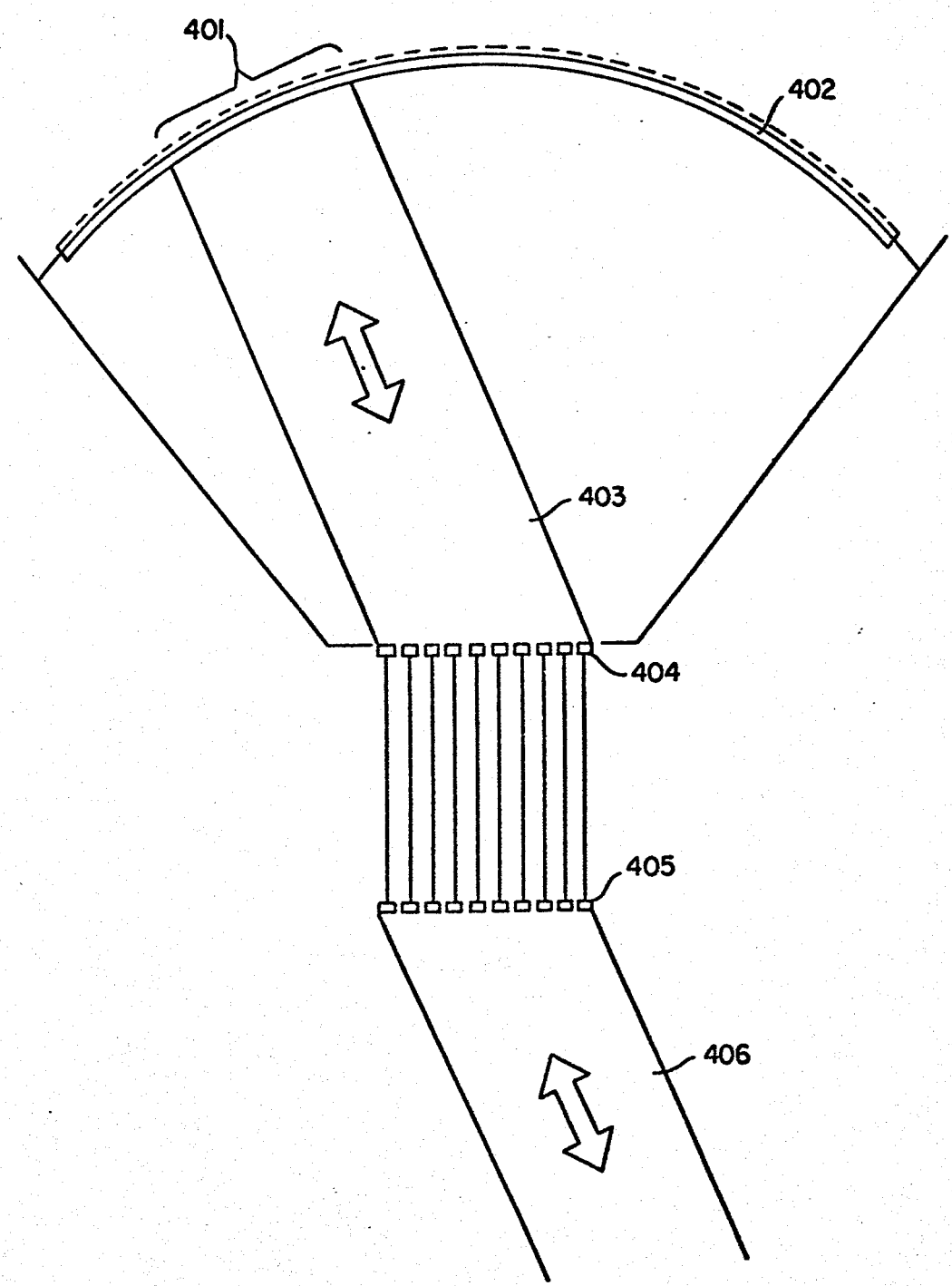
FIG. 26 shows the use according to the invention of an arcuate transducer system for producing a "phased array".

A further considerable reduction in the sound head can be obtained if the arc scanner is used not as a sound head but as a signal processor for a "phased array". This possibility is shown in FIG. 26. A group of transducers 401 comprising a number of segments of an arcuate transducer 402 transmits an ultrasonic beam 403 which, at the center of the arc, strikes a "phased array" 404 whose segments are disposed parallel to the segments of the arcuate transducer 404. By means of the phased array, the sound field is detected in segments in a phase-sensitive manner and transmitted to a second "phased array" 405; which forms the actual sound head, reconstructs the sound field at the site of the first "phased array" and radiates a corresponding ultrasound beam 406. Of course, the device can also be operated in the reverse direction, and is therefore suitable for transmission and reception. Advantageously, a transmitting and a receiving intermediate amplifier is disposed between the two "phased arrays" in each segment. For simplicity, these amplifiers were omitted in FIG. 26.

At this point it should be noted that the sound field radiated by the second "phased array" 405 need not be identical with the field detected by the first "phased array" 404. The phase and amplitude of the signals from each segment can be varied by the aforementioned intermediate amplifier. In addition, the second "phase array" 405 can be given a shape different from the first, thus altering the sound field. This provides an additional means of improving the focussing of the sound beam and thus improving the lateral resolution of the system.

The advantage of this device, compared with a traditional "phased array" system, is that the sound beam is angularly deflected by using simple means. Strictly speaking, this is applied mainly to operation as a receiver. During transmission, angular deflection can be obtained relatively easily by digital means, but complicated delay lines and switches have hitherto been required for reception. It is therefore better to use a hybrid solution, in which the "phased array" is directly operated during transmission and the arc scanner is used only as a received-signal processor.

Figure 27:
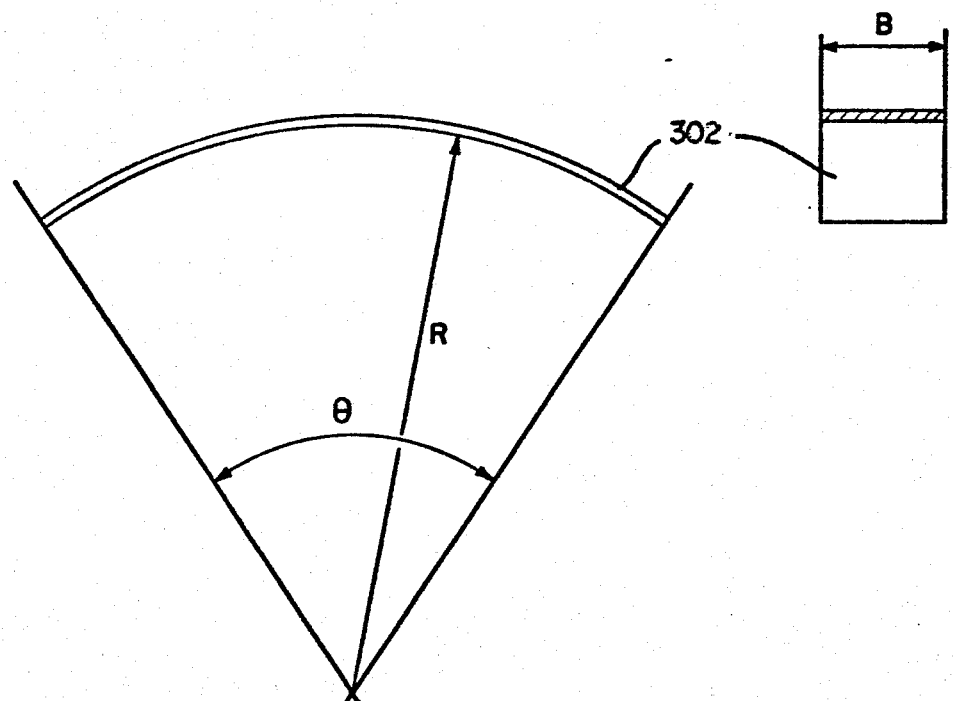
FIGS. 27 and 28 illustrate the dimensioning of an arcuate transducer system according to the invention.
Figure 28:
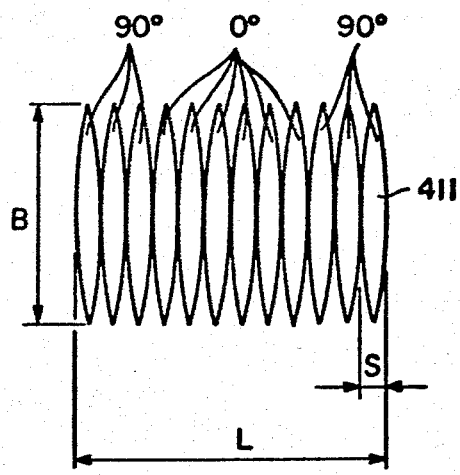

Finally, there is now described a simple example of an arc scanner for cardiological applications (FIGS. 27 and 28). The data for this signal are as follows:

| | |
|---|---|
| Frequency | 2 MHz |
| max. depth of penetration | 15 cm |
| angle to be scanned | 50-60° |
| number of segments | 64 |
| phases to be used | 0°, 90° |
| anticipatory path medium | water |
| focussing in one direction only | |

Under these boundary conditions, an optimization process was carried out, with reference to sound fields calculated by computer, and yielded the following dimensions.

As shown in FIG. 27, the transducer system 302 forms a portion of a cylinder. It has a radius R of 15 cm, a width B of 2 cm and an arc length 17.6 cm, corresponding to an angle $\theta = 67.2°$. The transducer is divided into 64 segments having a width S=2.75 mm. Twelve elements are used simultaneously for transmission and reception. One such group is shown in FIG. 28. The edges of the individual elements 411 are formed by arcs of a circle. This shape results in the desired apodisation and improvement of the beam shape. During transmission and reception, the signals from the outer six elements are made to lag 90° behind the signals for the inner six elements. This corresponds to focussing at a point about 25 cm from the transducer. At the same time, the signal amplitudes of the outer six elements during transmission and reception are multiplied by a factor of 0.5 and the signal amplitudes of the inner six elements are multiplied by a factor of unity.

By means of this transducer, a resolution of at least 4 mm is obtained in the scanning plane in the entire useful region. Owing to the absence of focussing, the resolution in the direction perpendicular thereto is lower by a factor of 1.5. As already mentioned, improved resolution in this direction also can be obtained by additional focussing.

What is claimed is:

1. An improved method of producing cross-sectional images using an ultrasonic imaging unit operating on the pulse-echo principle and comprising a transducer system having a stationary elongated array of adjacent transducer elements in which unit successively and cyclically selected groups of adjacent transducer elements of the transducer system are used to produce an ultrasonic beam in response to pulsed electric transmitter signals applied to the electrode segments, to transmit the ultrasonic beam, substantially in a scan plane, into a heterogeneous body, to receive echoes reflected from a discontinuity in the body, and to generate an electric echo signal in response to the received echoes, the transmitter signals applied to the transducer elements or element sub-assemblies and/or the echo signal given by the transducer elements or elements sub-assemblies being time-shifted with respect to one another, each transmitter or echo signal being associated with a time shift which is a function of the distance between the corresponding transducer element or element sub-assembly and the center of the group of transducer elements, such that in the case of adjacent transducer elements or element sub-assemblies, the transmitter signal and/or the time-shifted echo signal of the transducer element or element sub-assembly at the greater distance from the middle of the group of transducer elements has a phase lead with respect to the corresponding signal of the other element or element sub-assembly, wherein the improved method comprises:

weakly focussing the ultrasonic beam and/or the corresponding reception characteristic in the scan phase and over the examined depth within the body by means of said timeshifting of the transmitter and/or echo signals and optimizing the shape of the transmitted ultrasonic beam and/or the reception characteristic by weighting the amplitude of the transmitter and/or echo signals, each transmitter or echo signal of a transducer element or an element sub-assembly being assigned a weighting factor determined by a function of the distance between the transducer element or element sub-assembly and the center of the group of transducers.

2. An improved ultrasonic imaging unit for producing cross-sectional images, the unit comprising:

a timing generator for producing a pulsed electric timing signal;

a transducer system comprising a stationary elongated array of adjacent transducer elements, the transducer system being used to produce an ultrasonic beam in response to pulsed transmitter signals derived from the electric timing signal, to transmit the ultrasonic beam, substantially in a scan plane, into a heterogeneous body, to receive echoes reflected from a discontinuity in the body, and produce an electric echo signal in response to the received echos;

an element-counter selector device connected to the timing generator, the transducer system and an indicator device and used for successively and cyclically selecting groups of adjacent elements of the transducer system, applying the transmitter signals to the transducer elements of the selected group for generating the ultrasonic beam, and transmitting the echo signals produced by the group to the indicator device, which is used to convert the echo signals into a visible image reproducing the cross-sectional structure of the heterogeneous body; transmitter-signal generator means inserted between the timing generator and the element-counter selector device for deriving transmitter signals for the transducer elements or element sub-assemblies of the selected group of transducer elements, the transmitter signals obtained from the timing signal given by the timing generator being time-shifted with respect to one another and echo-signal receiver means inserted between the element-counter selector device and the indicator device for producing a relative time shift between the echo signal delivered by the transducer elements or element sub-assemblies of the group of transducers the phase angle ($\phi$) of the transmitter signals or the time-shifted echo signals being so determined by a function of the distance between the corresponding transducer element and the center of the group of transducer elements that, in the case of adjacent transducer elements or element sub-assemblies, the transmitter signal and/or the time-shifted echo signal of the transducer element or element sub-assembly at the greater distance from the middle of the group of transducer elements has a phase lead with respect to the corresponding signal of the other element or element sub-assembly, wherein the improvement is characterized in that the time-shifted signals serve for generating an ultrasonic beam and/or a corresponding reception characteristic which is weakly focussed over the examined depth within the body and that the transmitter and/or the receiver means include means for weighting the transmitter and/or echo signals to optimize the shape of the ultrasonic beam and/or the reception characteristic, each transmitter or echo signal from a transducer element or an element sub-assembly being assigned a weighting factor determined by a function of the distance between the transducer element or element sub-assembly and the center of the group of transducer elements.

3. A device according to claim 2 wherein the transmitter-signal generator delivers transmitter signals of varying amplitude, and the transmitter signals having the higher amplitudes are applied to the inner transducer elements or element sub-assemblies of each selected group.

4. A device according to claim 2 wherein the echo-signal receiver includes a weighting circuit which is used to associate various weighting factors with the amplitude of the echo signals delivered by the transducer elements or element sub-assemblies, the echo signals from the inner transducer elements being given higher weighting factors.

5. A device according to claim 2 wherein the group of transducers successively connected by the element-counter selector device alternately contain an even and an odd number of transducer elements, successive groups being formed alternately by reducing the number of transducer elements in one direction and increasing the number of transducer elements in the opposite direction.

6. A device according to claim 2 wherein the time shift between transmitter signals for adjacent transducer elements or element sub-assemblies and/or the time shift between the echo signals, time-shifted with respect to one another, from adjacent transducer elements of element sub-assemblies at different distances from the center of the group of transducer elements corresponds to a phase shift of a high-frequency carrier wave contained in each transmitter or echo signal, the absolute value of the phase shift lying in the region between 30° and 180°.

7. A device according to claim 6 wherein the time shift in both cases is approximately equal to a phase shift having an absolute value of 90°.

8. A device according to claim 6 wherein the time shift between the transmitter signals and the time shift between the echo signals correspond to different phase shifts.

9. A device according to claim 8, characterized by the following combination of the absolute values of the phase shift between transmitter signals for and between the echo signals, time-shifted with respect to one another, from adjacent transducer elements or element sub-assemblies:

| Transmitter-signals | Echo-signals |
|---|---|
| Approx 90° | Approx 45° |
| Approx 45° | Approx 90° |

10. A device according to claim 2 wherein the intersection of the radiating surface of the transducer system with any plane perpendicular to the scan plane and parallel to the transmitted ultrasonic beam has such a curvature that the radiating surface weakly focusses the ultrasonic beam and the corresponding reception characteristic also in said plane perpendicular to the scan plane.

11. A device according to claim 10 wherein instead of the curvature of the radiating surface the transducer elements are flat and segmented along their longitudinal axis into a top, a middle and a bottom part, the top and bottom parts of the outer element segments of the radiating group of transducers not being used either for transmission or reception, and the transmitter signals for the top and bottom parts of the inner element segments being phase-shifted compared with the transmitter signals for the middle parts of the same element segments and/or have a lower amplitude.

12. An improved method of producing cross-sectional images using an ultrasonic imaging unit operating on the pulse-echo principle and comprising a transducer system having a stationary elongated array of adjacent transducer elements, in which unit successively and cyclically selected groups of adjacent transducer elements of the transducer system are used to produce an ultrasonic beam in response to pulsed electric transmitter signals applied to the transducer elements, to transmit the ultrasonic beam, substantially in a scan plane, into a heterogenous body, to receive echoes reflected from a discontinuity in the body, and to generate an electric echo signal in response to the received echoes, the transmitter signals applied to the transducer elements or element sub-assemblies and/or the echo signals given by the transducer elements or element sub-assemblies being time-shifted with respect to one another, each transmitter of echo signal being associated with a time shift which is a function of the distance between the corresponding transducer element or element sub-assembly and the center of the group of transducer elements such that in the case of adjacent transducer elements or element sub-assemblies, the transmitter signal and/or the time-shifted echo signal of the transducer element or the element sub-assembly at the greater distance from the middle of the group of transducer elements has a phase lead with respect to the corresponding signal of the other element or element sub-assembly, wherein the improved method comprises:
aspherically focussing the ultrasonic beam and/or the corresponding reception characteristic in the scan plane by means of said time shifting of the transmitter and/or echo signals, aspherically focussing the ultrasonic beam and/or the corresponding reception characteristic also in planes perpendicular to the scan plane and optimizing the shape of the transmitted ultrasonic beam and/or the reception characteristic by weighting the amplitude of the transmitter and/or echo signals, each transmitter of echo signal from the transducer element or an element sub-assembly being assigned a weighting factor determined by a function of the distance between the transducer element or element sub-assembly and the center of the group of transducer elements.

13. An improved ultrasonic imaging unit for producing cross-sectional images, the unit comprising:
a timing generator for producing a pulsed electric timing signal;
a transducer system comprising a stationary elongated array of adjacent transducer elements, the transducer system being used to produce an ultrasonic beam in response to pulsed transmitter signals derived from the electric timing signal, to transmit the ultrasonic beam, substantially in a scan plane, into a heterogeneous body, to receive echoes reflected from a discontinuity in the body, and produce an electric echo signal in response to the received echoes;
an element-counter selector device connected to the timing generator, the transducer system and an indicator device and used for successively and cyclically selecting groups of adjacent elements of the transducer system, applying the transmitter signals to the transducer elements of the selected group for generating the ultrasonic beam, and transmitting the echo signals produced by the group to the indicator device, which is used to convert the echo signals into a visible image reproducing the cross-sectional structure of the heterogeneous body;
transmitter-signal generator means inserted between the timing generator and the element-counter selector device for deriving transmitter signals for the transducer elements or element sub-assemblies of the selected group of transducer elements, the transmitter signals obtained from the timing signal given by the timing generator being time-shifted with respect to one another, and
echo-signal receiver means inserted between the element-counter selector device and the indicator derive for producing a relative time shift between the echo signal delivered by the transducer elements or element sub-assemblies of the group of transducer elements;
the phase angle ($\phi$) of the transmitter signals or the time-shifted echo signals being so determined by a function of the distance between the corresponding transducer element or element sub-assembly and the center of the group of transducer elements that, in the case of adjacent transducer elements or element sub-assemblies, the transmitter signal and/or the time-shifted echo signal of the transducer element or element sub-assembly at the greater distance from the middle of the group of transducer elements has a phase lead with respect to the corresponding signal of the other element or element sub-assembly, wherein the improvement is characterized in that the time-shifted signals serve for generating an ultrasonic beam and/or a reception characteristic which is aspherically focussed in the scan plane, that the intersection of the radiating surface of the transducer system with any plane perpendicular to the scan plane and parallel to the transmitted ultrasonic beam has such a curvature that the radiating surface aspherically focusses the ultrasonic beam and the corresponding reception characteristic also in said plane perpendicular to the scan plane, and that the transmitter and/or the receiver means include means for weighting the transmitter and/or echo signals to optimize the shape of the ultrasonic beam and/or the reception characteristic, each transmitter or echo signal from a transducer element or an element sub-assembly being assigned a weighting factor determined by a function of the distance between the transducer element or element sub-assembly and the center of the group of transducer elements.

14. A device according to claim 13 wherein the phase angle ($\phi$) of the transmitter signals and/or the time-shifted echo signals increases stepwise in linear manner with the distance of the corresponding transducer element or element sub-assembly from the center of the group of transducer elements.

15. A device according to claim 13 wherein the phase angle ($\phi$) of the transmitter signals or the time-shifted echo signals increases stepwise and approximately in accordance with a hyperbolic function with the distance between the corresponding transducer elements or element sub-assembly and the center of the transducer element group.

16. A device according to claim 13 wherein the phase angle of the transmitter signals or the time-shifted echo signals increases stepwise with the distance between the corresponding transducer element or element sub-assembly and the center of the group of transducer elements, the increase being quadratic towards the center of the group of transducer elements and linear at the edge regions.

17. A device according to claim 13 wherein the transmitter signal generator delivers transmitter signals of varying amplitude, and the transmitter signals having the higher amplitudes are applied to the inner transducer elements or element sub-assemblies of each selected group.

18. A device according to claim 13 wherein the echo-signal receiver includes a weighting circuit which is used to associate various weighting factors with the amplitude of the echo signals delivered by the transducer elements or element sub-assemblies, the echo signals from the inner transducer elements being given higher weighting factors.

19. A device according to claim 13 wherein the group of transducers successively connected by the element-counter selector device alternately contain an even and an odd number of transducer elements, successive groups being formed alternately by reducing the number of transducer elements in one direction and increasing the number of transducer elements in the opposite direction.

20. A device according to claim 13 wherein the radiating surface of the transducer system appears as an approximately V-shaped line in a cross-section lying in a plane at right angles to the longitudinal axis of radiating surface.

21. A device according to claim 20 wherein the V-shaped line is made up of two straight segments.

22. A device according to claim 20 wherein the V-shaped line is approximately hyperbolical.

23. A device according to claim 13 wherein instead of the curvature of the radiating surface the transducer elements are flat and segmented along their longitudinal axis into a top, a middle and a bottom part, the top and bottom parts of the outer element segments of the radiating group of transducers not being used either for transmission or reception, and the transmitter signals for the top and bottom parts of the inner element segments being phase-shifted compared with the transmitter signals for the middle parts of the same element segments and/or have a lower amplitude.

24. A device according to claim 13 wherein the time shift between transmitter signals for adjacent transducer elements or element sub-assemblies and/or the time shift between the echo signals, time-shifted with respect to one another, from adjacent transducer elements or element sub-assemblies at different distances from the center of the group of transducer elements correspond to a phase shift of a high-frequency carrier wave contained in each transmitter or echo signal, the absolute value of the phase shift lying in the region between 30° and 180°.

25. A device according to claim 24 wherein the time shift in both cases is approximately equal to a phase shift having an absolute value of 90°.

26. A device according to claim 24 wherein the time shift between the transmitter signals and the time shift between the echo signals correspond to different phase shifts.

27. A device according to claim 26, characterized by the following combination of the absolute values of the phase shift between transmitter signals for and between the echo signals, time-shifted with respect to one another, from adjacent transducer elements or element sub-assemblies:

| Transmitter signals | Echo signals |
| --- | --- |
| Approx 90° | Approx. 45° |
| Approx 45° | Approx 90° |

28. An improved ultrasonic imaging unit for producing cross-sectional images, which unit operates on the pulse-echo principle and comprises a transducer system having a stationary elongated array of adjacent transducer elements, in which unit successively and cyclically selected groups of adjacent transducer elements or element sub-assemblies of the transducer system are used to produce an ultrasonic beam in response to pulsed electric transmitter signals applied to the transducer elements, to transmit the ultrasonic beam, substantially in a scan plane, and/or to receive ultrasonic echoes and to generate an electric echo signal in response to the received echoes, said transducer array being arcuate in the scan plane and serving for generating a rotating beam by means of the cyclical selection of groups of adjacent transducer elements to perform a sector scanning in a transmission region and/or for receiving echoes derived by performing a sector scanning in that region, and an anticipatory path provided between the transducer system and the transmission region, the anticipatory path being comprised within a closed envelope, wherein the improved unit is characterized in that it comprises: a second and a third array of transducer elements, each element of the second array being electrically connected to a corresponding element of the third array, in which unit the centre of the second array is placed at the centre of the arc corresponding to the shape of the transducer system, the elements of the second array substantially face the elements of the transducer system and the second array is arranged to receive an ultrasonic beam generated by a group of elements of the transducer system and to transmit electrical signals corresponding to said beam to the third array, which thereupon radiates a corresponding ultrasonic beam, or to receive electrical signals corresponding to echo waves received by the third array and to transmit an ultrasonic beam corresponding to the latter electrical signals to a group of transducer elements of the transducer system.

29. A device according to claim 28 wherein the elements of the transducer device comprise a radiating surface which becomes progressively narrower in the direction at right angles to the scanning direction and outwardly from the longitudinal axis of the transducer system.

30. A device according to claim 29 wherein the edges of the individual elements are formed by arcs.

31. A device according to claim 28 wherein the distance between the arcuate transducer device and the focus of the ultrasonic field produced thereby is approximately equal to the length of the anticipatory path in the transmission medium plus approximately ⅔ of the maximum imaging depth.

32. A device according to claim 28 wherein in order to weakly focus the ultrasonic beam produced by each group of transducers, the transmitter signals applied to the transducer elements or element sub-assemblies and/or the echo signals from the transducer elements of element sub-assemblies are phase-shifted with respect to one another, each transmitter or echo signal being associated with a phase shift which is a function of the distance between the corresponding transducer element or element sub-assembly and the center of the group of transducer elements.

33. A device according to claim 32, wherein the phase angle ($\phi$) of the transmit signal or of the time-shifted echo signals is so determined by a function of the distance between the corresponding transducer element or element sub-assembly and the center of the group of transducer that, in the case of adjacent transducer elements or element sub-assemblies, the transmitter signal and/or the time-shifted echo signal of the transducer element or element sub-assembly which is at the greater distance from the center of the group of transducer elements has a phase lag with respect to the corresponding signal of the other element or element sub-assembly.

* * * * *